(12) United States Patent
Anzai et al.

(10) Patent No.: US 12,288,328 B2
(45) Date of Patent: Apr. 29, 2025

(54) BLOOD FLOW FIELD ESTIMATION APPARATUS, LEARNING APPARATUS, BLOOD FLOW FIELD ESTIMATION METHOD, AND PROGRAM

(71) Applicant: TOHOKU UNIVERSITY, Sendai (JP)

(72) Inventors: Hitomi Anzai, Sendai (JP); Kazuhiro Watanabe, Sendai (JP); Gaoyang Li, Sendai (JP); Makoto Ohta, Sendai (JP); Teiji Tominaga, Sendai (JP); Kuniyasu Niizuma, Sendai (JP); Shinichiro Sugiyama, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 352 days.

(21) Appl. No.: 17/798,870

(22) PCT Filed: Feb. 22, 2021

(86) PCT No.: PCT/JP2021/006654
§ 371 (c)(1),
(2) Date: Aug. 10, 2022

(87) PCT Pub. No.: WO2021/172280
PCT Pub. Date: Sep. 2, 2021

(65) Prior Publication Data
US 2023/0046302 A1     Feb. 16, 2023

(30) Foreign Application Priority Data
Feb. 28, 2020   (JP) .................................. 2020-033293

(51) Int. Cl.
*G06T 7/187*       (2017.01)
*A61B 5/02*        (2006.01)
(Continued)

(52) U.S. Cl.
CPC .. *G06T 7/0012* (2013.01); *G06T 2207/20081* (2013.01); *G06T 2207/20084* (2013.01)

(58) Field of Classification Search
USPC .................. 128/920, 922–925; 382/154–173; 706/1–62, 900–903, 920, 924
See application file for complete search history.

(56) References Cited

U.S. PATENT DOCUMENTS

| 7,738,685 | B2 * | 6/2010 | Hyun | ..................... G06T 7/187 |
| | | | | 382/128 |
| 8,908,939 | B2 * | 12/2014 | Bredno | .................. A61B 6/507 |
| | | | | 382/128 |

(Continued)

FOREIGN PATENT DOCUMENTS

JP     2015-531264 A    11/2015
JP     2017-535340 A    11/2017
(Continued)

OTHER PUBLICATIONS

Office Action received in corresponding JP Application No. 2020-033293, mailed Oct. 31, 2023, in 6 pages, with translation.
(Continued)

*Primary Examiner* — Marcellus J Augustin
(74) *Attorney, Agent, or Firm* — PROCOPIO, CORY, HARGREAVES & SAVITCH LLP

(57) ABSTRACT

A blood flow field estimation apparatus is provided, including an estimation unit that uses a learned model obtained in advance by performing machine learning to learn a relationship between organ tissue three-dimensional structure data including image data of a plurality of organ cross-sectional images serving as cross-sectional images of an organ and having each pixel provided with two or more bit depths and image position information serving as information indicating a position of an image reflected on each of the organ cross-sectional images in the organ, and a blood flow field in
(Continued)

the organ, and estimates the blood flow field in the organ of an estimation target, based on the organ tissue three-dimensional structure data of the organ of the estimation target, and an output unit that outputs an estimation result of the estimation unit.

6 Claims, 7 Drawing Sheets

(51) Int. Cl.
*A61B 5/0205* (2006.01)
*A61B 5/026* (2006.01)
*G06T 7/00* (2017.01)

(56) References Cited

U.S. PATENT DOCUMENTS

| | | | |
|---|---|---|---|
| 9,087,147 B1* | 7/2015 | Fonte | A61B 5/0263 |
| 2014/0247970 A1* | 9/2014 | Taylor | A61B 34/25 |
| | | | 382/128 |
| 2015/0310299 A1* | 10/2015 | Goto | G06F 18/2413 |
| | | | 382/128 |
| 2017/0245821 A1* | 8/2017 | Itu | A61B 6/504 |
| 2019/0336084 A1 | 11/2019 | Grady et al. | |
| 2022/0280423 A1* | 9/2022 | Nedergaard | A61K 9/0085 |

FOREIGN PATENT DOCUMENTS

| | | |
|---|---|---|
| JP | 6539736 B | 7/2019 |
| JP | 2019-532702 A | 11/2019 |
| WO | 2014/042899 A2 | 3/2014 |
| WO | 2016/075331 A2 | 5/2016 |

OTHER PUBLICATIONS

Philipp Fischer, et al., "FlowNet: Learning Optical Flow with ConvolutionalNetworks", 2015 [retrieved on Jan. 23, 2020] Internet <URL : https://arxiv.org/pdf/1504.06852.pdf>.

N. Thuerey, et al., "Deep Learning Methods for Reynolds-Averaged Navier-StokesSimulations of Airfoil Flows", 2020 [retrieved on Jan. 23, 2020] Internet <URL : https://arxiv.org/pdf/1810.08217.pdf>.

Xiaoxiao Guo, Wei Li, Francesco Iorio, "Convolutional Neural Networks for SteadyFlow Approximation", 2016 [retrieved on Jan. 23, 2020] Internet <URL : https://www.researchgate.net/profile/Xiaoxiao_Guo7/publication/305997840_Convolutional_Neural_Networks_for_Steady_Flow_Approximation/links/5c1404b8a6fdcc494ff510a3/Convolutional-Neural-Networks-for-Steady-Flow-Approximation.pdf>.

International Search Report mailed on Apr. 13, 2021, from International Application No. PCT/JP2021/006654, 4 pages.

* cited by examiner

BLOOD FLOW FIELD ESTIMATION APPARATUS, LEARNING APPARATUS, BLOOD FLOW FIELD ESTIMATION METHOD, AND PROGRAM

CROSS-REFERENCE TO RELATED APPLICATIONS

This application is a U.S. National Stage entry of PCT Application No: PCT/JP2021/006654 filed Feb. 22, 2021, which claims priority to Japanese Patent Application No. 2020-033293 filed Feb. 28, 2020, the contents of which are incorporated herein by reference.

TECHNICAL FIELD

The present invention relates to a blood flow field estimation apparatus, a learning apparatus, a blood flow field estimation method, and a program.

BACKGROUND ART

As the performance of computers has improved in recent years, techniques that were previously not possible have been realized in various ways, and have been used in many situations. As such techniques, a prediction technique using a neural network (Non-Patent Documents 1 to 3) or a prediction technique using computer simulation is known.

For example, the prediction technique using the neural network has started to be used in an automatic translation system. On the other hand, for example, the technique using the computer simulation has been used in medical fields to estimate a blood flow field in the brain, which is important for detecting or predicting a disease such as a stroke. The blood flow field is a distribution of hydrodynamic physical quantities relating to blood flow such as the velocity, shear rate, and vorticity inside a blood vessel. For example, a simulation method for estimating the blood flow field in the brain includes a method for analyzing vascular computational fluid dynamics (CFD).

CITATION LIST

Non-Patent Documents

Non-Patent Document 1

Philipp Fischer, et al., "FlowNet: Learning Optical Flow with Convolutional Networks", [Searched Jan. 23, 2020], Internet <URL: https://arxiv.org/pdf/1504.06852.pdf>

Non-Patent Document 2

N. Thuerey, et al., "Deep Learning Methods for Reynolds-Averaged Navier-Stokes Simulations of Airfoil Flows", [Searched Jan. 23, 2020], Internet <URL: https://arxiv.org/pdf/1810.08217.pdf>

Non-Patent Document 3

Xiaoxiao Guo, Wei Li, Francesco Iorio, "Convolutional Neural Networks for Steady Flow Approximation", [Search on Jan. 23, 2020], Internet <URL: https://www.researchgate.net/profile/Xiaoxiao_Guo7/publication/305997840_Convolutional_Neural_Networks_for_Steady_Flow_Approximation/links/5c14 04b8a6fdcc4-94ff510a3/Convolutional-Neural-Networks-for-Steady-Flow-Approximation.pdf>

SUMMARY OF INVENTION

Technical Problem

However, in estimating the blood flow field in the brain using computer simulation, it is necessary to perform processing on a measurement result image such as computed tomography (CT) image or magnetic resonance imaging (MM) of the brain before the simulation starts. Specifically, a complicated process is required for processing the measurement result image into an image suitable for the simulation. For example, one of the processes is a process for binarizing the image to separately show the blood vessel and other tissues. One of the processes is a process for reconstructing a three-dimensional image of the brain, based on a CT image of the brain. One of the processes is a process for smoothing a surface of the blood vessel. For example, one of the processes is a process for properly setting a calculation grid.

In this way, since a complicated process is required in advance, estimating the blood flow field in the brain may be burdensome for a person estimating the blood flow field in some cases. In addition, such a burden on the person estimating the blood flow field is a problem common not only to the brain but also to an organ since a complicated process is required in advance.

In view of the above-described circumstances, an object of the present invention is to provide a technique for reducing a burden when a blood flow field in an organ is estimated.

Solution to Problem

According to an aspect of the present invention, a blood flow field estimation apparatus is provided, including an estimation unit that uses a learned model obtained in advance by performing machine learning to learn a relationship between organ tissue three-dimensional structure data including image data of a plurality of organ cross-sectional images serving as cross-sectional images of an organ and having each pixel provided with two or more bit depths and image position information serving as information indicating a position of an image reflected on each of the organ cross-sectional images in the organ, and a blood flow field in the organ, and estimates the blood flow field in the organ of an estimation target, based on the organ tissue three-dimensional structure data of the organ of the estimation target, and an output unit that outputs an estimation result of the estimation unit.

In the blood flow field estimation apparatus according to the aspect of the present invention, in the organ, fluid characteristics of blood vessels may be substantially the same as each other regardless of the estimation target.

In the blood flow field estimation apparatus according to the aspect of the present invention, the organ may be a brain.

In the blood flow field estimation apparatus according to the aspect of the present invention, the machine learning may be deep learning.

In the blood flow field estimation apparatus according to the aspect of the present invention, a method of the deep learning may be a U-Net method.

In the blood flow field estimation apparatus according to the aspect of the present invention, the estimation unit may divide the organ tissue three-dimensional structure data into a plurality of partial data serving as data satisfying a partial condition, and thereafter, may estimate the blood flow field in the organ of the estimation target by using the learned model for each of the partial data, and the partial condition may include a condition that the partial data is partial information of the organ tissue three-dimensional structure data, a condition that the partial data indicates a pixel value at each position of a partial space in the organ out of pixel values indicated by the organ tissue three-dimensional structure data, and a condition that information indicated by a sum of all of the divided partial data is the same as information indicated by the organ tissue three-dimensional structure data.

According to another aspect of the present invention, a learning apparatus is provided, including a learning unit that uses teacher data in which an explanatory variable is organ tissue three-dimensional structure data including image data of a plurality of organ cross-sectional images serving as cross-sectional images of an organ and having each pixel provided with two or more bit depths and image position information serving as information indicating a position of an image reflected on each of the organ cross-sectional images in the organ, and an objective variable is data indicating an organ blood flow field in the organ indicated by the organ tissue three-dimensional structure data, and that performs machine learning to learn a relationship between the organ tissue three-dimensional structure data including the image data of the plurality of organ cross-sectional images serving as the cross-sectional images of the organ and having the two or more bit depths of each pixel and the image position information serving as the information indicating the position of the image reflected on each of the organ cross-sectional images in the organ, and the blood flow field in the organ, and a model output unit that outputs a learning result of the learning unit.

According to still another aspect of the present invention, a blood flow field estimation method is provided, including an estimation step of using a learned model obtained in advance by performing machine learning to learn a relationship between organ tissue three-dimensional structure data including image data of a plurality of organ cross-sectional images serving as cross-sectional images of an organ and having each pixel provided with two or more bit depths and image position information serving as information indicating a position of an image reflected on each of the organ cross-sectional images in the organ, and a blood flow field in the organ, and estimating the blood flow field in the organ of an estimation target, based on the organ tissue three-dimensional structure data of the organ of the estimation target, and an output step of outputting an estimation result obtained by the estimation step.

According to still another aspect of the present invention, a program is provided for operating a computer to function as the blood flow field estimation apparatus.

According to still another aspect of the present invention, a program is provided for operating a computer to function as the learning apparatus.

Advantageous Effects of Invention

According to the present invention, it is possible to reduce a burden when the blood flow field in the organ is estimated.

DESCRIPTION OF EMBODIMENT

Embodiment

Figure 1:
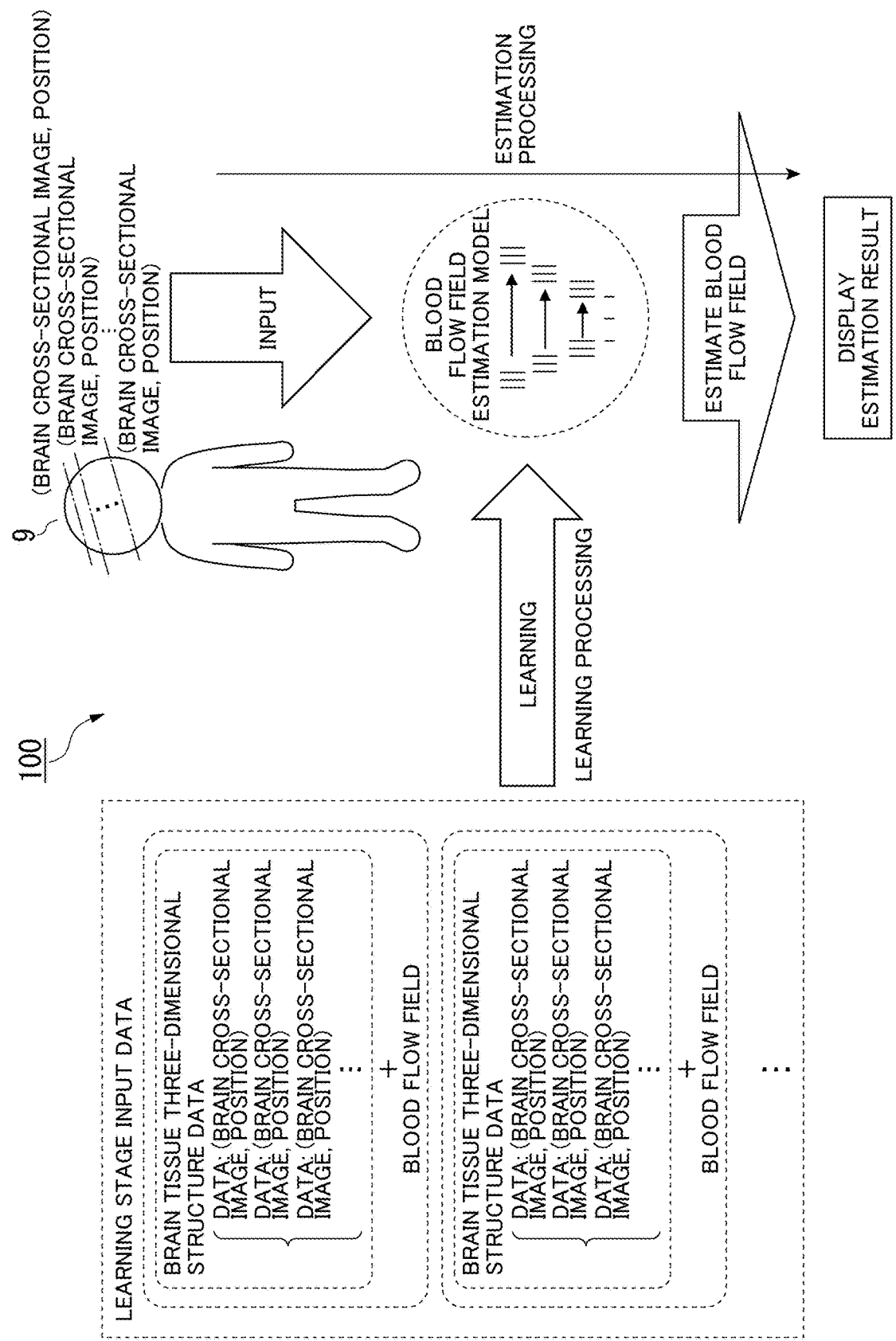
FIG. 1 is a diagram describing an outline of a blood flow field estimation system 100 according to an embodiment.

FIG. 1 is a diagram describing an outline of a blood flow field estimation system 100 according to an embodiment. The blood flow field estimation system 100 performs a learning process and an estimation process. The learning process is a process for performing machine learning to learn a relationship between brain tissue three-dimensional structure data and a blood flow field in a brain and generating a learned model (hereinafter, referred to as a "blood flow field estimation model"). The blood flow field is a distribution of hydrodynamic physical quantities relating to a blood flow such as the velocity, shear rate, and vorticity inside a blood vessel. The brain tissue three-dimensional structure data is information including image data of a plurality of brain cross-sectional images having each pixel provided with two or more bit depths, and information indicating a position of an image reflected on each brain cross-sectional image in the brain (hereinafter, referred to as "image position information"). The brain cross-sectional image is a brain cross-sectional image serving as an image obtained so that a brain cross section is imaged by using a predetermined imaging method, and having each pixel provided with two or more bit depths.

The predetermined imaging method may be any method as long as a plurality of brain cross-sectional images can be acquired, and for example, may be computed tomography (CT) or magnetic resonance imaging (MM). A data format of the brain cross-sectional image may be any format as long as the brain cross-sectional image can be expressed, and for example, the brain cross-sectional image may be an image having a format of digital imaging and communications in medicine (DICOM).

More specifically, the blood flow field estimation system 100 generates a blood flow field estimation model by performing deep learning using data satisfying the following teacher data conditions (hereinafter, referred to as "learning stage input data") as teacher data. The teacher data conditions include the condition that an explanatory variable is the brain tissue three-dimensional structure data. The teacher data conditions include the condition that an objective variable is the information indicating a blood flow field in a brain indicated by the brain tissue three-dimensional structure data of the corresponding explanatory variable (hereinafter, referred to as "pre-acquired blood flow field information").

For example, the pre-acquired blood flow field information is data acquired in advance by a computer simulation such as blood flow computational fluid dynamics (CFD) analysis or a predetermined measurement method for measuring the blood flow field. For example, the predetermined measurement method for measuring the blood flow field is phase contrast-magnetic resonance imaging (PC-MM). For example, the predetermined measurement method for measuring the blood flow field may be 4 dimensional-magnetic resonance (4D-MR). For example, the predetermined measurement method for measuring the blood flow field may be 4 dimensional-digital subtraction angiography (4D-DSA), an Optical Flow, or an ultrasonic Doppler method.

The blood flow field estimation model may be any model as long as a learned model can obtain a relationship between the brain tissue three-dimensional structure data and the blood flow field in the brain by using a machine learning method. For example, the machine learning method may be deep learning. For example, the deep learning may be a convolutional neural network (CNN) method. In this case, the blood flow field estimation model is a learned model in which the relationship between the brain tissue three-dimensional structure data and the blood flow field in the brain is learned by using the CNN method. For example, the deep learning may be a U-Net method. In this case, the blood flow field estimation model is a learned model in which the relationship between the brain tissue three-dimensional structure data and the blood flow field in the brain is learned by using the U-Net method. The U-Net method has a process of classifying and a process of creating an image, and the neural network automatically learns the process of creating the image from a classification result. As a result, the U-Net method can output a result in a state where humans are likely to understand the result. In this way, the U-Net method is superior to the CNN method for performing only classification in that the image is created by the neural network.

The U-Net method is a type of encoder/decoder model, and can obtain output data having the same size as that of input data. In the U-Net method, information used in an encoder is used in a decoder layer. This means that a feature map during encoding is coupled with up-sampled information by using skip coupling. Therefore, in the U-Net method, a feature amount can be extracted while position information is held, and high-definition segmentation is available.

Up-sampling means increasing a dimension of internal data. Increasing the dimension of the internal data means significantly restoring an array size. The reason for the up-sampling is as follows. The U-Net method includes an operation for decreasing the dimension (that is, decreasing the array size) as layers are stacked. Therefore, the up-sampling is performed so that an output data size returns to an original size. The operation for decreasing the dimension is called max pooling. In this way, the up-sampling is performed in the U-Net method to restore the dimension as the layers are stacked.

When the U-Net method is used in the blood flow field estimation system 100, data input to the learned model is three-dimensional data. Accordingly, first, an operation for halving each of vertical and horizontal depths is repeated in the U-Net method. Next, in the U-Net method, an operation for doubling the vertical and horizontal depths to return to the original size is repeated. The data input to the learned model is brain tissue three-dimensional structure data.

Of the advantageous effects of the U-Net method, with regard to an advantageous effect by which output data having the same size as that of input data can be achieved, the same advantageous effect can be achieved as long as the neural network causes an encoder/decoder to be executed.

The estimation process is a process for estimating the blood flow field in the brain of an estimation target person 9 by using the generated blood flow field estimation model, based on the brain tissue three-dimensional structure data of the brain of the estimation target person 9. The blood flow field estimation system 100 displays the blood flow field in the brain which is estimated by performing the estimation process.

Figure 2:
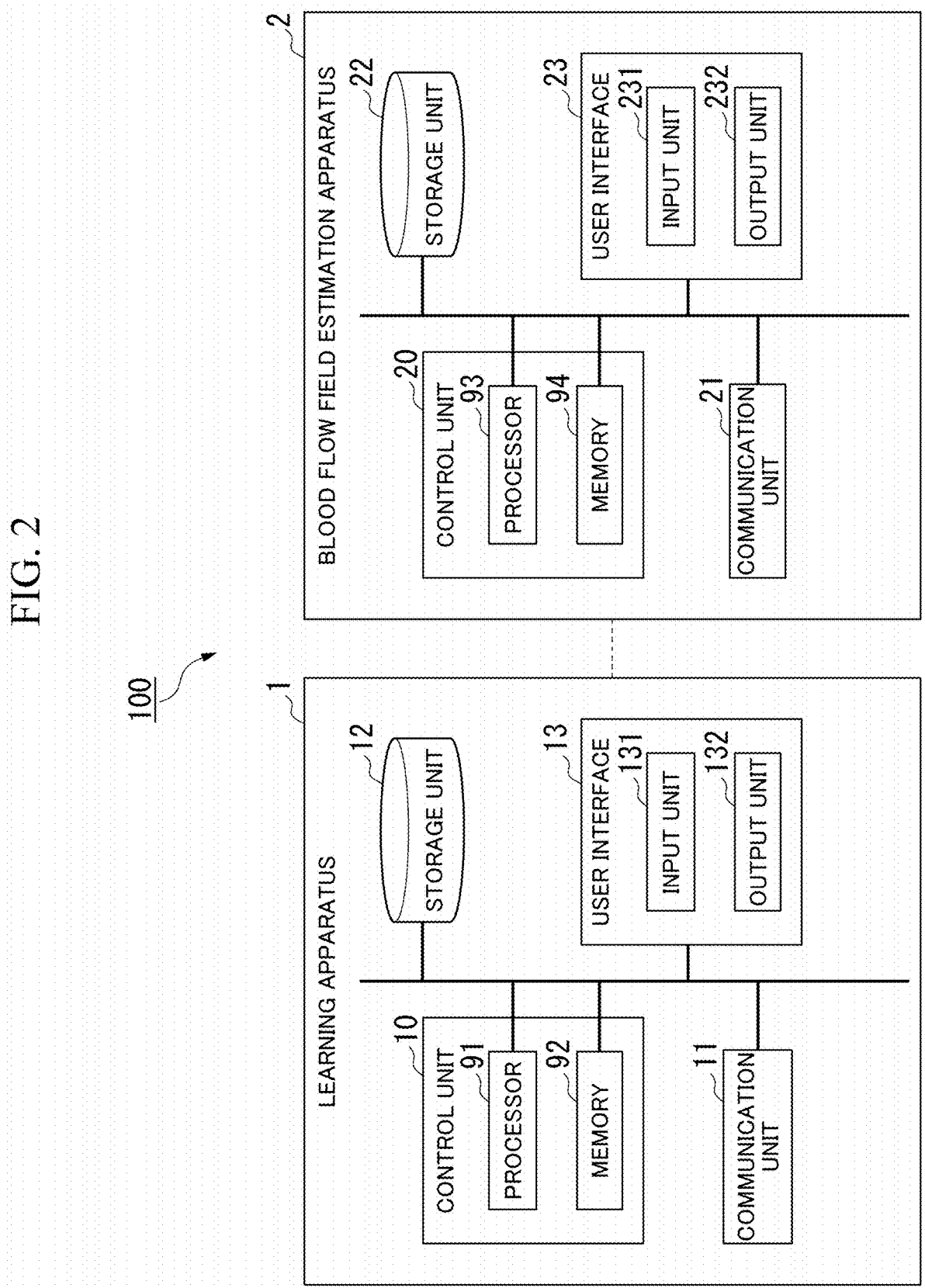
FIG. 2 is a diagram representing an example of a hardware configuration of the blood flow field estimation system 100 in the embodiment.

FIG. 2 is a diagram representing an example of a hardware configuration of the blood flow field estimation system 100 in the embodiment. The blood flow field estimation system 100 includes a learning apparatus 1 and a blood flow field estimation apparatus 2.

The learning apparatus 1 performs a learning process. The learning apparatus 1 includes a control unit 10 including a processor 91 such as a central processing unit (CPU) connected by a bus and a memory 92, and executes a program. The learning apparatus 1 functions as an apparatus including the control unit 10, a communication unit 11, a storage unit 12, and a user interface 13 by executing a program.

More specifically, in the learning apparatus 1, the processor 91 reads a program stored in the storage unit 12, and stores the read program in the memory 92. The processor 91 executes the program stored in the memory 92 so that the learning apparatus 1 functions as the apparatus including the control unit 10, the communication unit 11, the storage unit 12, and the user interface 13.

The control unit 10 controls an operation of each functional unit included in a host apparatus (learning apparatus 1). For example, the control unit 10 generates a blood flow field estimation model by performing a learning process. For example, the control unit 10 records the generated blood flow field estimation model in the storage unit 12. For example, the control unit 10 controls an operation of the communication unit 11. For example, the control unit 10 controls the operation of the communication unit 11 to transmit the blood flow field estimation model to the blood flow field estimation apparatus 2.

The communication unit 11 is configured to include a communication interface for connecting the learning apparatus 1 to the blood flow field estimation apparatus 2. For example, the communication unit 11 transmits the blood flow field estimation model to the blood flow field estimation apparatus 2 serving as a communication destination.

The storage unit 12 is configured by using a storage device such as a magnetic hard disk device and a semiconductor storage device. The storage unit 12 stores various information relating to the learning apparatus 1. For example, the storage unit 12 stores a program for controlling the operation of each functional unit included in the learning apparatus 1 in advance. For example, the storage unit 12 stores the blood flow field estimation model.

The user interface 13 includes an input unit 131 that receives an input to the learning apparatus 1 and an output unit 132 that displays various information relating to the learning apparatus 1. For example, the user interface 13 is a touch panel. The input unit 131 receives an input to the host apparatus. The input unit 131 is an input terminal such as a mouse, a keyboard, and a touch panel. For example, the input unit 131 may be configured to serve as an interface for connecting the input terminals to the host apparatus. For example, the output unit 132 is a display device such as a liquid crystal display and an organic electro luminescence (EL) display. For example, the output unit 132 may be configured to serve as an interface for connecting the display devices to the host apparatus. For example, the output unit 132 may be an audio output device such as a speaker. For example, the input received by the input unit 131 is learning stage input data.

The blood flow field estimation apparatus 2 performs an estimation process. The blood flow field estimation apparatus 2 includes a control unit 20 including a processor 93 such as a CPU connected by a bus and a memory 94, and executes a program. The blood flow field estimation apparatus 2 functions as an apparatus including the control unit 20, the communication unit 21, the storage unit 22, and the user interface 23 by executing a program.

More specifically, in the blood flow field estimation apparatus 2, the processor 93 reads a program stored in the storage unit 22, and stores the read program in the memory 94. The processor 93 executes the program stored in the memory 94 so that the blood flow field estimation apparatus 2 functions as an apparatus including the control unit 20, the communication unit 21, the storage unit 22, and the user interface 23.

The control unit 20 controls the operation of each functional unit included in the host apparatus (blood flow field estimation apparatus 2). For example, the control unit 20 estimates the blood flow field in the brain of the estimation target person 9 by performing the estimation process. For example, the control unit 20 outputs an estimation result to the user interface 23. For example, the control unit 20 records the estimation result in the storage unit 22. For example, the control unit 20 controls the operation of the communication unit 21. For example, the control unit 20 controls the operation of the communication unit 21, and receives the blood flow field estimation model transmitted by the learning apparatus 1.

The communication unit 21 is configured to include a communication interface for connecting the blood flow field estimation apparatus 2 to the learning apparatus 1. For example, the communication unit 21 receives the blood flow field estimation model transmitted by the learning apparatus 1 serving as a communication destination.

The storage unit 22 is configured by using a storage device such as a magnetic hard disk device and a semiconductor storage device. The storage unit 22 stores various information relating to the blood flow field estimation apparatus 2. For example, the storage unit 22 stores a program for controlling the operation of each functional unit included in the blood flow field estimation apparatus 2 in advance. For example, the storage unit 22 stores the blood flow field estimation model. For example, the storage unit 22 stores the estimation result of the estimation process.

The user interface 23 includes an input unit 231 that receives an input to the blood flow field estimation apparatus 2 and an output unit 232 that displays various information relating to the blood flow field estimation apparatus 2. For example, the user interface 23 is a touch panel. The input unit 231 receives an input to the host apparatus. The input unit 231 is an input terminal such as a mouse, a keyboard, and a touch panel. For example, the input unit 231 may be configured to serve as an interface for connecting the input terminals to the host apparatus. For example, the output unit 232 is a display device such as a liquid crystal display and an organic electro luminescence (EL) display. For example, the output unit 232 may be configured to serve as an interface for connecting the display devices to the host apparatus. For example, the output unit 232 may be an audio output device such as a speaker. For example, the input received by the input unit 231 is the brain tissue three-dimensional structure data of the brain of the estimation target person 9. For example, the output unit 232 displays the estimation result of the estimation process.

Figure 3:
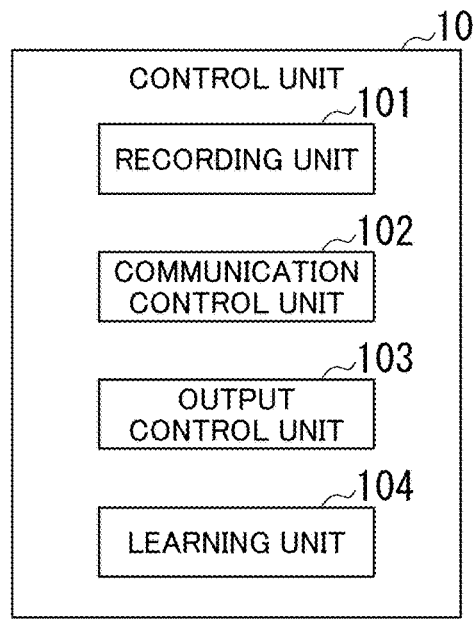
FIG. 3 is a diagram representing an example of a functional configuration of a control unit 10 in the embodiment.

FIG. 3 is a diagram representing an example of a functional configuration of the control unit 10 in the embodiment. The control unit 10 includes a recording unit 101, a communication control unit 102, an output control unit 103, and a learning unit 104.

The recording unit 101 records information in the storage unit 12. The communication control unit 102 controls the operation of the communication unit 11. The output control unit 103 controls the operation of the output unit 132.

The learning unit 104 performs the learning process. More specifically, the learning unit 104 performs deep learning, based on the learning stage input data input via the input unit 131. The learning unit 104 generates the blood flow field estimation model by performing deep learning based on the learning stage input data.

Figure 4:
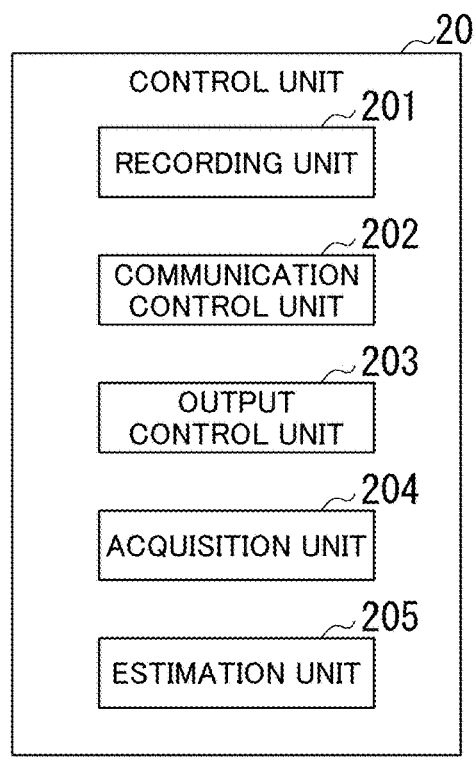
FIG. 4 is a diagram representing an example of a functional configuration of a control unit 20 in the embodiment.

FIG. 4 is a diagram representing an example of a functional configuration of the control unit 20 in the embodiment. The control unit 20 includes a recording unit 201, a communication control unit 202, an output control unit 203, an acquisition unit 204, and an estimation unit 205.

The recording unit 201 records information in the storage unit 22. The communication control unit 202 controls the operation of the communication unit 21. The output control unit 203 controls the operation of the output unit 232. The acquisition unit 204 acquires the brain tissue three-dimensional structure data of the brain of the estimation target person 9 input via the input unit 231.

The estimation unit 205 performs the estimation process. More specifically, the estimation unit 205 estimates the blood flow field in the brain of the estimation target person 9 by using the blood flow field estimation model, based on the brain tissue three-dimensional structure data acquired by the acquisition unit 204.

Figure 5:
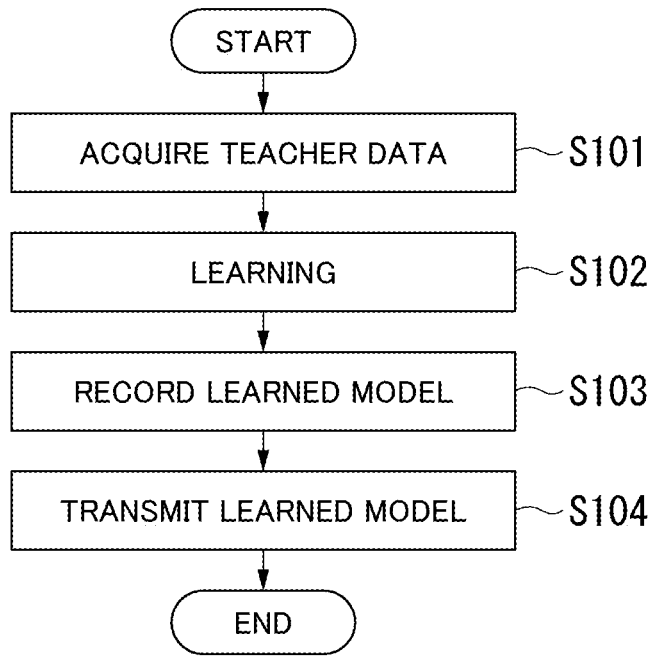
FIG. 5 is a flowchart representing an example of a flow of a process performed by a learning apparatus 1 in the embodiment.

FIG. 5 is a flowchart representing an example of a flow of a process performed by the learning apparatus 1 in the embodiment.

The user interface 13 acquires the learning stage input data (Step S101). Specifically, the fact that the user interface 13 acquires the learning stage input data means that the learning stage input data is input to the user interface 13. Subsequently to Step S101, the learning unit 104 performs learning, based on the input learning stage input data (Step S102). The learning unit 104 generates the blood flow field estimation model by performing learning. Specifically, the learning unit 104 uses deep learning in which an explanatory variable is the brain tissue three-dimensional structure data in the learning stage input data and an objective variable is the pre-acquired blood flow field information in the learning stage input data, and generates the blood flow field estimation model. Subsequently to Step S102, the recording unit 101 records the generated blood flow field estimation model in the storage unit 12 (Step S103). Next, the communication control unit 102 transmits the generated blood flow field estimation model to the blood flow field estimation apparatus 2 by controlling the operation of the communication unit 11.

Figure 6:
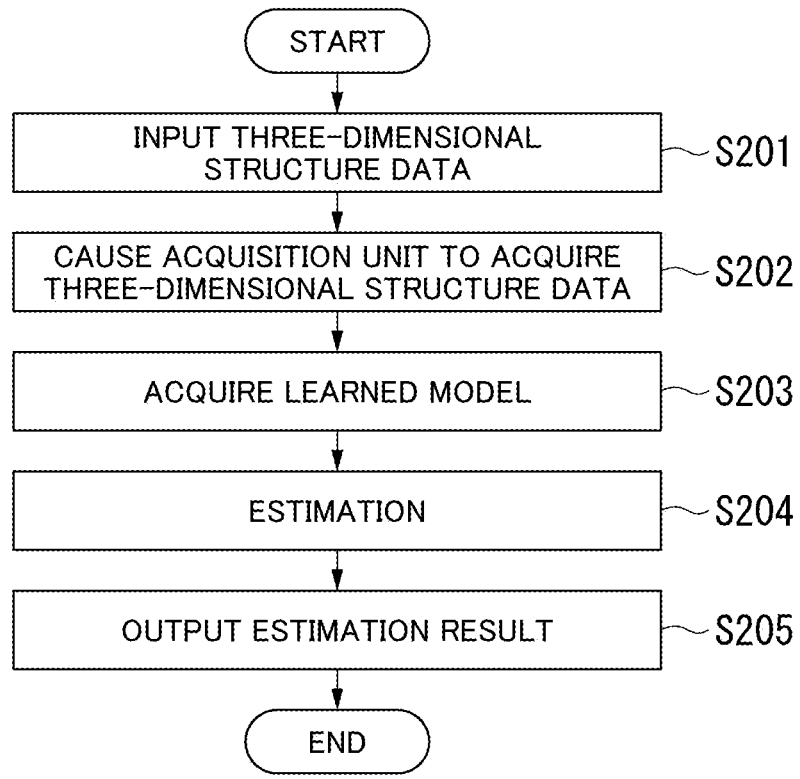
FIG. 6 is a flowchart representing an example of a flow of a process performed by a blood flow field estimation apparatus 2 in the embodiment.

FIG. 6 is a flowchart representing an example of a flow of a process performed by the blood flow field estimation apparatus 2 in the embodiment.

The user interface 23 acquires the brain tissue three-dimensional structure data of the brain of the estimation target person 9 (Step S201). Specifically, the fact that the user interface 23 acquires the brain tissue three-dimensional structure data of the brain of the estimation target person 9 means that the brain tissue three-dimensional structure data of the brain of the estimation target person 9 is input to the user interface 23.

Subsequently to Step S201, the acquisition unit 204 acquires the input brain tissue three-dimensional structure data (Step S202). Next, the communication control unit 202 acquires the blood flow field estimation model from the learning apparatus 1 via the communication unit 21 by controlling the operation of the communication unit 21 (Step S203). Next, the estimation unit 205 estimates the blood flow field in the brain of the estimation target person 9 by using the blood flow field estimation model, based on the brain tissue three-dimensional structure data of the brain of the estimation target person 9 (Step S204). Next, the output control unit 203 outputs the estimation result of the blood flow field in the brain of the estimation target person 9 to the output unit 232 by controlling the operation of the output unit 232 (Step S205).

(Experiment Result)

Hereinafter, an example of an experiment result will be described with reference to FIGS. 7 to 12 in comparison with a measurement result (that is, pre-acquired blood flow field information). The blood flow field in the brain represented in FIGS. 7 to 12 has a magnitude of a component parallel to an X-axis direction, a component parallel to a Y-axis direction, and a component parallel to a Z-axis direction of a velocity vector of a blood flow. FIGS. 7 to 12 represent DICOM images. The DICOM images in FIGS. 7 to 12 are images representing the blood flow in a location having a high luminance value. The location having the blood flow is a location having a blood vessel.

Figure 7:
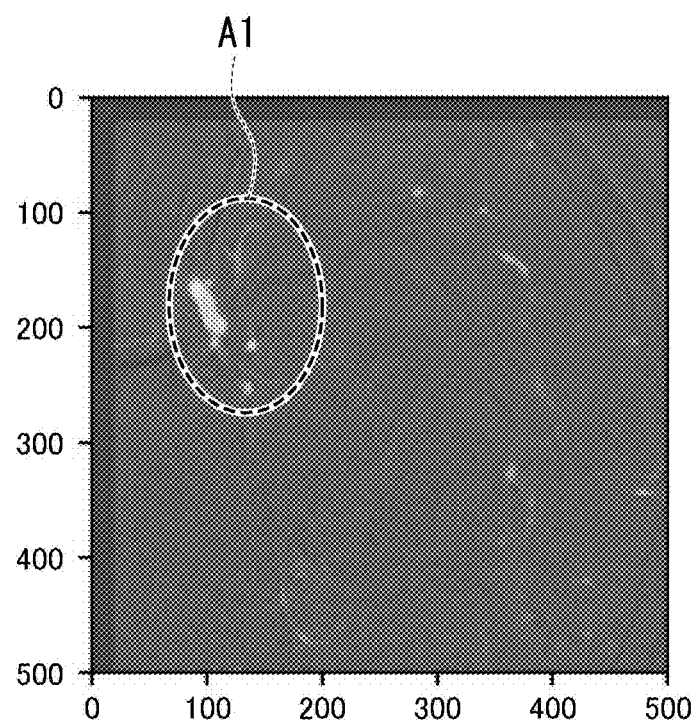
FIG. 7 is a first diagram representing an example of a measurement result in an experiment in which a blood flow field in a brain of an estimation target person 9 is estimated by using the blood flow field estimation system 100 according to the embodiment.
Figure 8:
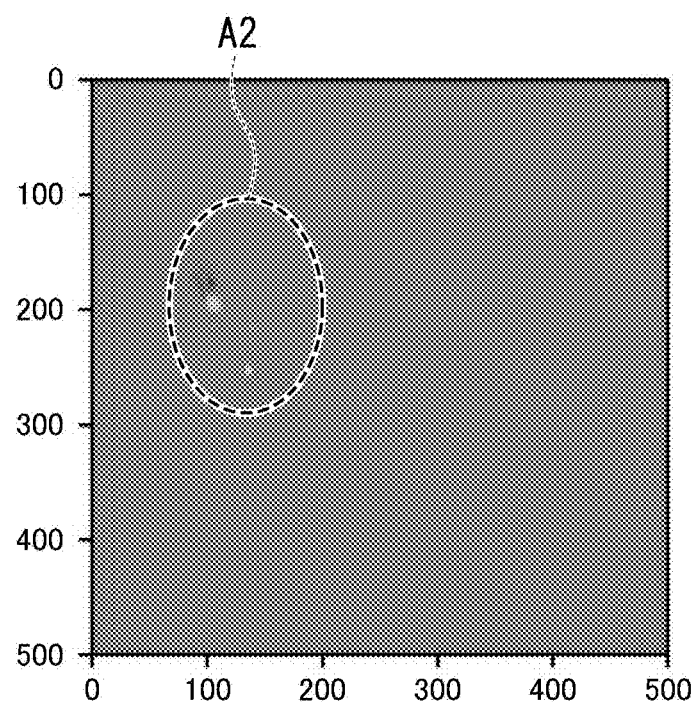
FIG. 8 is a first diagram representing an example of an estimation result in the experiment in which the blood flow field in the brain of the estimation target person 9 is estimated by using the blood flow field estimation system 100 according to the embodiment.
Figure 9:
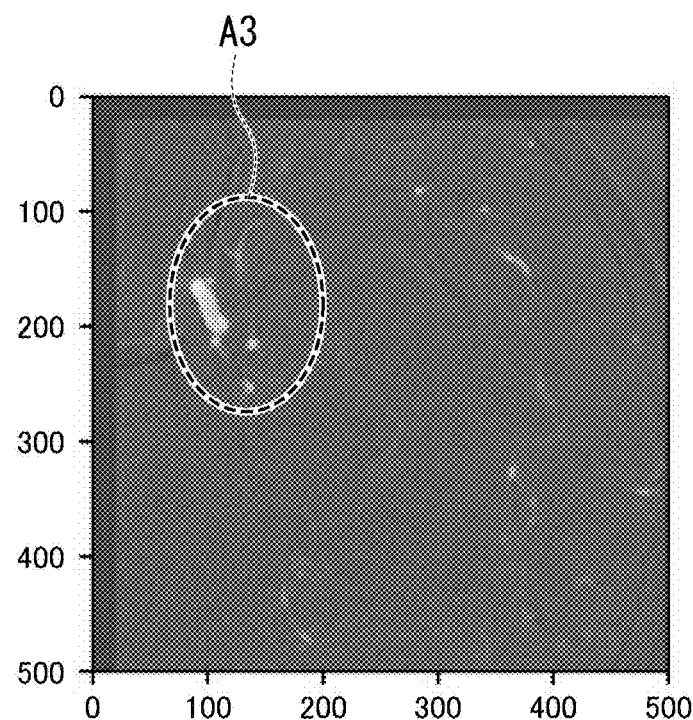
FIG. 9 is a second diagram representing an example of a measurement result in the experiment in which the blood flow field in the brain of the estimation target person 9 is estimated by using the blood flow field estimation system 100 according to the embodiment.
Figure 10:
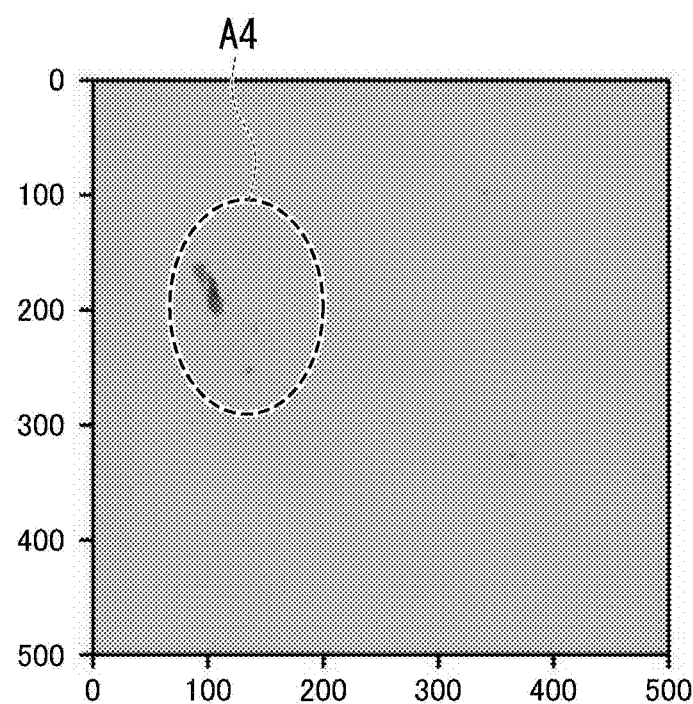
FIG. 10 is a second diagram representing an example of an estimation result in an experiment in which the blood flow field in the brain of the estimation target person 9 is estimated by using the blood flow field estimation system 100 according to the embodiment.
Figure 11:
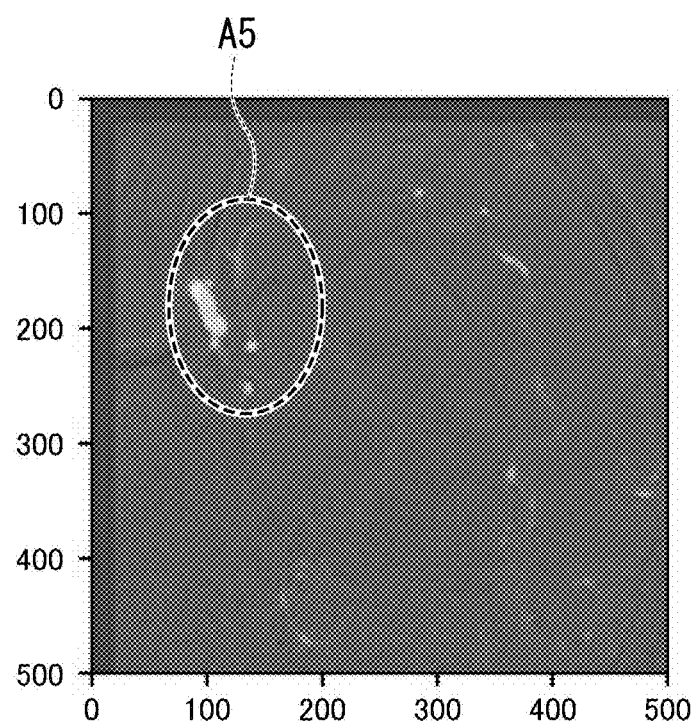
FIG. 11 is a third diagram representing an example of a measurement result in the experiment in which the blood flow field in the brain of the estimation target person 9 is estimated by using the blood flow field estimation system 100 according to the embodiment.
Figure 12:
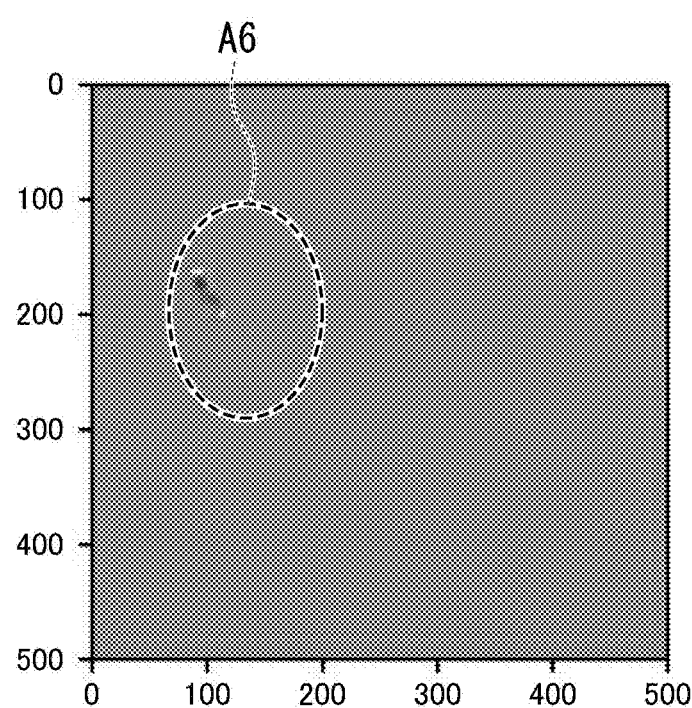
FIG. 12 is a third diagram representing an example of an estimation result in the experiment in which the blood flow field in the brain of the estimation target person 9 is estimated by using the blood flow field estimation system 100 according to the embodiment.

FIGS. 7, 9, and 11 represent the measurement results in the experiment. The experiment results of FIGS. 7, 9, and 11 respectively represent a magnitude of the component parallel to the X-axis direction, the component parallel to the Y-axis direction, and the component parallel to the Z-axis direction of the velocity vector of the measured blood flow. A method for measuring the velocity of the blood flow is a blood flow CFD analysis. FIGS. 8, 10, and 12 represent the estimation results of the blood flow field estimation system 100 in the experiment. The experiment results in FIGS. 8, 10, and 12 respectively represent a magnitude of the component parallel to the X-axis direction, the component parallel to the Y-axis direction, and the component parallel to the Z-axis direction of the velocity vector of the blood flow of the estimation results.

FIG. 7 is a first diagram representing an example of a measurement result in an experiment in which the blood flow field of the estimation target person 9 is estimated by using the blood flow field estimation system 100 according to the embodiment.

FIG. 7 is an example of pre-acquired blood flow field information indicating a distribution of the flow velocity of the blood flow in the X-axis direction in one cross section in the brain of the estimation target person 9. A unit of a vertical axis and a horizontal axis in FIG. 7 is a pixel. An enclosure A1 in FIG. 7 indicates that there is a position where the flow velocity is faster than the flow velocity at other positions. In addition, a length of one pixel on the horizontal axis and the vertical axis in FIG. 7 is 0.227 mm.

FIG. 8 is a first diagram representing an example of an estimation result in an experiment in which the blood flow field in the brain of the estimation target person 9 is estimated by using the blood flow field estimation system 100 according to the embodiment.

FIG. 8 is an example of an estimation result representing a distribution of the flow velocity in the X-axis direction in one cross section in the brain of the estimation target person 9. The unit of the vertical axis and the horizontal axis in FIG. 8 is a pixel. An enclosure A2 in FIG. 8 indicates that there is a position where the flow velocity is faster than the flow velocity at other positions. FIG. 8 represents that the distribution of the flow velocity of the blood flow is close to the result in FIG. 7. In addition, the length of one pixel on the horizontal axis and the vertical axis in FIG. 8 is 0.227 mm.

FIG. 9 is a second diagram representing an example of a measurement result in an experiment in which the blood flow field in the brain of the estimation target person 9 is estimated by using the blood flow field estimation system 100 according to the embodiment.

FIG. 9 is an example of pre-acquired blood flow field information indicating a distribution of the flow velocity in the Y-axis direction in one cross section in the brain of the estimation target person 9. The unit of the vertical axis and the horizontal axis in FIG. 9 is a pixel. An enclosure A3 in FIG. 9 indicates that there is a position where the flow velocity is faster than the flow velocity at other positions. In addition, the length of one pixel on the horizontal axis and the vertical axis in FIG. 9 is 0.227 mm.

FIG. 10 is a second diagram representing an example of an estimation result in an experiment in which the blood flow field in the brain of the estimation target person 9 is estimated by using the blood flow field estimation system 100 according to the embodiment.

FIG. 10 is an example of an estimation result indicating a distribution of the flow velocity in the Y-axis direction in one cross section in the brain of the estimation target person 9. The unit of the vertical axis and the horizontal axis in FIG. 10 is a pixel. An enclosure A4 in FIG. 10 indicates that there is a position where the flow velocity is faster than the flow velocity at other positions. FIG. 10 represents that the distribution of the flow velocity of the blood flow is close to the result in FIG. 9. In addition, the length of one pixel on the horizontal axis and the vertical axis in FIG. 10 is 0.227 mm.

FIG. 11 is a third diagram representing an example of a measurement result in an experiment in which the blood flow field in the brain of the estimation target person 9 is estimated by using the blood flow field estimation system 100 according to the embodiment.

FIG. 11 is an example of pre-acquired blood flow field information indicating a distribution of the flow velocity in the Z-axis direction in one cross section in the brain of the estimation target person 9. The unit of the vertical axis and the horizontal axis in FIG. 11 is a pixel. An enclosure A5 in FIG. 11 indicates that there is a position where the flow velocity is faster than the flow velocity at other positions. In addition, the length of one pixel on the horizontal axis and the vertical axis in FIG. 11 is 0.227 mm.

FIG. 12 is a third diagram representing an example of an estimation result in an experiment in which the blood flow field in the brain of the estimation target person 9 is estimated by using the blood flow field estimation system 100 according to the embodiment.

FIG. 12 is an example of an estimation result indicating a distribution of the flow velocity in the Z-axis direction in one cross section in the brain of the estimation target person 9. The unit of the vertical axis and the horizontal axis in FIG. 12 is a pixel. An enclosure A6 in FIG. 12 indicates that there is a position where the flow velocity is faster than the flow velocity at other positions. FIG. 12 represents that the distribution of the flow velocity of the blood flow is close to the result in FIG. 11. In addition, the length of one pixel on the horizontal axis and the vertical axis in FIG. 12 is 0.227 mm.

As indicated by the results in FIGS. 7 to 12, the blood flow field estimation system 100 estimates a result close to the measurement result.

The blood flow field estimation system 100 configured in this way estimates the blood flow field in the brain of the estimation target person 9 by using a learned model generated in advance, based on unprocessed brain tissue three-dimensional structure data which is the brain tissue three-dimensional structure data of the brain of the estimation target person 9. Therefore, a person estimating the blood flow field in the brain of the estimation target person 9 does not need to process the data (that is, the brain tissue three-dimensional structure data) input to the blood flow field estimation system 100 in advance. Therefore, the blood flow field estimation system 100 can reduce a burden on the person when analyzing the blood flow field in the brain.

In addition, in the blood flow field estimation system 100 configured in this way, one pixel of the brain cross-sectional image has two or more bit depths. The fact that one pixel has two or more bit depths means that the amount of information is larger than that when the brain cross-sectional image has one bit depth. Therefore, the blood flow field estimation system 100 can more accurately estimate the blood flow field, compared to a case of using the brain cross-sectional image in which one pixel has one bit depth.

<Reason that Blood Flow Field Estimation System 100 does not Require Prior Processing when Estimating Blood Flow Field>

A reason that the blood flow field estimation system 100 does not require prior processing when estimating the blood flow field will be described.

An equation governing an uncompressed and isothermal CFD analysis is an equation continuous with the Navier-Stokes equation. Blood can be assumed to be uncompressed and isothermal in a living environment. Accordingly, the blood flow field is uniquely determined, based on the law of flow, when a shape of a fluid region, a boundary condition, and fluid characteristics are determined. It is known that a difference in results of the blood flow CFD which are obtained by different numerical analysis software is not large.

In the blood flow CFD, it is necessary to set a three-dimensional fluid region. In particular, when a shape of the fluid region having a patient's specific shape is set from a medical image, a threshold value is set for a luminance value indicated by a two-dimensional cross-sectional image, and tissues are divided, based on the set threshold value. Then, each of divided two-dimensional regions is stacked at a predetermined interval in a direction perpendicular to each of the two-dimensional regions. As a result, a shape of a three-dimensional fluid region is obtained. Therefore, luminance value information indicated by the brain cross-sectional image includes information on the shape of the three-dimensional fluid region.

In addition, in the blood flow CFD, in many cases, the fluid characteristics are not measurement values, and are provided as substantially the same without depending on patients.

In this way, the brain cross-sectional image includes information on a shape and a boundary condition required for the blood flow CFD. Therefore, in the blood flow CFD in which the fluid characteristics are substantially the same without depending on patients, the brain cross-sectional image is subjected to mapping of the flow field.

The blood flow field estimation system 100 estimates the blood flow field in the brain by using a learned model learned through machine learning. The learned model generated through the machine learning is a non-linear model, and is a numerical model in which regions outside the fluid region to which a flow equation is not applied are also incorporated into the calculation. In the learned model, the blood flow field based on voxels in the fluid region and the flow equation, and the blood flow field when there is no voxel and no flow outside the fluid region are learned in association with each other. Therefore, the blood flow field in the brain can be estimated for all elements inside an input three-dimensional arrangement. Therefore, the person estimating the blood flow field in the brain by using the blood flow field estimation system 100 does not designate the fluid region or does not designate the boundary condition for the brain tissue three-dimensional structure data, and can acquire the estimation result of the blood flow field in the brain.

Modification Example

The blood flow field estimation model is not necessarily acquired by the blood flow field estimation apparatus 2 at a timing in Step S203 as long as the estimation unit 205 can be used when the process in Step S204 is performed. For example, the blood flow field estimation model may be recorded in the storage unit 22 in advance before the brain tissue three-dimensional structure data of the brain of the estimation target person 9 is input to the user interface 23. For example, the blood flow field estimation model may be acquired by being read from the storage unit 12 included in the learning apparatus 1 via the communication unit 21 at a timing of using the blood flow field estimation model when the process in Step S204 is performed.

A timing for the learning apparatus 1 to transmit the blood flow field estimation model to the blood flow field estimation apparatus 2 may be after the blood flow field estimation model is generated, and may be any timing as long as the timing is before the timing for the blood flow field estimation apparatus 2 to use the blood flow field estimation model.

The estimation unit 205 may divide the brain tissue three-dimensional structure data into a plurality of partial data by using image position information included in the brain tissue three-dimensional structure data, and thereafter, may estimate the blood flow field in the brain by using the blood flow field estimation model for each partial data. The partial data is data satisfying the following partial condition. The partial condition includes a condition that the partial condition is partial information on the brain tissue three-dimensional structure data. The partial condition includes a condition that the partial condition indicates a pixel value at each position in a partial space in the brain out of pixel values indicated by the brain tissue three-dimensional structure data. The partial condition includes a condition that information indicated by a sum of all of the divided partial data is the same as information indicated by the brain tissue three-dimensional structure data.

When the blood flow field in the brain is estimated for each partial data after the brain tissue three-dimensional structure data is divided into the plurality of partial data, the blood flow is independently estimated for each partial data regardless of information of other partial data. Therefore, the blood flow field estimation apparatus 2 that estimates the blood flow field in the brain for each partial data after the brain tissue three-dimensional structure data is divided into the plurality of partial data can perform the estimation processes in parallel to estimate the blood flow field in the brain for the plurality of partial data. Therefore, a calculation time required for the estimation can be shortened.

The brain tissue three-dimensional structure data may be any information as long as the data is information obtained so that a pixel value of the image in the brain, an image in which each pixel has two or more bit depths, is indicated for each position in the brain. For example, the brain tissue three-dimensional structure data may be a three-dimensional image reconstructed in advance, based on the two-dimensional image.

The blood flow field estimated by the blood flow field estimation system 100 is not necessarily limited to the blood flow field in the brain. The blood flow field estimated by the blood flow field estimation system 100 may be a blood flow field in any organ as long as the blood flow field is located in the organ. In particular, accuracy is improved in the estimation of the blood flow field estimation system 100 as the fluid characteristics of the blood vessel in the organ are substantially the same regardless of the estimation target. Therefore, it is desirable that the organ for which the blood flow field estimation system 100 estimates the blood flow field is an organ in which the fluid characteristics are substantially the same regardless of the estimation target. The brain is an example of an organ in which the fluid characteristics are substantially the same regardless of the estimation target. The blood flow field estimated by the blood flow field estimation system 100 may be a blood flow field in an abdominal aorta, may be a blood flow field in a coronary artery, or may be a blood flow field in limbs.

The estimation target for which the blood flow field estimation system 100 estimates the blood flow field is not limited to a human. The estimation target for which the blood flow field estimation system 100 estimates the blood flow field may be an animal other than a human.

A machine learning method for generating the blood flow field estimation model may be a fully convolutional network (FCN) having no skip coupling such as the U-Net method. In addition, for example, the machine learning method for generating the blood flow field estimation model may be a pyramid scene parsing network (PSPNet), or may be a SegNet. However, when the U-Net method is used, a feature amount and position information can be held as described above. Therefore, a boundary between the blood vessel and the outside of the blood vessel is clear, and the flow velocity can be calculated only in the fluid region.

The communication unit 11 may be configured to include an interface for connection to an external storage device such as a universal serial bus (USB) memory that stores the blood flow field estimation model. In this case, the communication unit 11 may output the blood flow field estimation model to the external storage device serving as a connection destination. The communication unit 11 is an example of the model output unit. The recording unit 101 outputs and stores the blood flow field estimation model in the storage unit 12, and thus, is an example of the model output unit.

The blood flow field estimation model is an example of the learning result. The brain cross-sectional image is an example of the organ cross-sectional image. The brain tissue three-dimensional structure data is an example of the organ tissue three-dimensional structure data.

The learning apparatus 1 and the blood flow field estimation apparatus 2 may be mounted by using a plurality of information-processing apparatuses connected to be communicable via a network. In this case, each functional unit included in the learning apparatus 1 and the blood flow field estimation apparatus 2 may be distributed and mounted in the plurality of information-processing apparatuses.

The learning apparatus 1 and the blood flow field estimation apparatus 2 are not necessarily mounted as different apparatuses. For example, the learning apparatus 1 and the blood flow field estimation apparatus 2 may be mounted as one apparatus having both functions.

Each function of the learning apparatus 1 and the blood flow field estimation apparatus 2 may be partially or entirely realized by using hardware such as an application-specific integrated circuit (ASIC), a programmable logic device (PLD), and a field-programmable gate array (FPGA). The program may be recorded on a computer-readable recording medium. For example, the computer-readable recording medium is a portable medium such as a flexible disk, a magneto-optical disk, a ROM, and a CD-ROM, or a storage device such as a hard disk built in a computer system. The program may be transmitted via a telecommunication line.

Hitherto, the embodiment of the present disclosure has been described in detail with reference to the drawings. However, a specific configuration is not limited to the embodiment, and includes a design change within the scope not departing from the concept of the present disclosure.

REFERENCE SIGNS LIST

1: Learning apparatus
2: Blood flow field estimation apparatus
9: Estimation target person
100: Blood flow field estimation system
10: Control unit
11: Communication unit
12: Storage unit
13: User interface
131: Input unit
132: Output unit
20: Control unit
21: Communication unit
22: Storage unit
23: User interface
231: Input unit
232: Output unit
101: Recording unit
102: Communication control unit
103: Output control unit 104: Learning unit
201: Recording unit
202: Communication control unit
203: Output control unit
204: Acquisition unit
205: Estimation unit

What is claimed is:

1. A blood flow field estimation apparatus, comprising:
a processor; and
a storage medium having computer program instructions stored thereon, wherein the computer program instructions, when executed by the processor, perform:
by using a learned model obtained in advance by performing machine learning to learn a relationship between organ tissue three-dimensional structure data including image data of a plurality of organ cross-sectional images serving as cross-sectional images of an organ and having each pixel provided with two or more bit depths and image position information serving as information indicating a position of an image reflected on each of the organ cross-sectional images in the organ, and a blood flow field in the organ, estimating the blood flow field in the organ of an estimation target, based on the organ tissue three-dimensional structure data of the organ of the estimation target;
outputting an estimation result of the estimation,
dividing the organ tissue three-dimensional structure data into a plurality of partial data serving as data satisfying a partial condition; and
estimating the blood flow field in the organ of the estimation target by using the learned model for each of the partial data,
wherein the partial condition includes a condition that the partial data is partial information of the organ tissue three-dimensional structure data, a condition that the partial data indicates a pixel value at each position of a partial space in the organ out of pixel values indicated by the organ tissue three-dimensional structure data, and a condition that information indicated by a sum of all of the divided partial data is the same as information indicated by the organ tissue three-dimensional structure data.

2. The blood flow field estimation apparatus according to claim 1,
wherein in the organ, fluid characteristics of blood vessels are substantially the same as each other regardless of the estimation target.

3. The blood flow field estimation apparatus according to claim 2,
wherein the organ is a brain.

4. The blood flow field estimation apparatus according to any one of claim 1,
wherein a method of the machine learning is deep learning.

5. The blood flow field estimation apparatus according to claim 4,
wherein a method of the deep learning is a U-Net method.

6. A non-transitory computer readable medium which stores a program for operating a computer to function as the blood flow field estimation apparatus according to claim 1.

* * * * *